US00PP25036P3

(12) United States Plant Patent
Villegas

(10) Patent No.: US PP25,036 P3
(45) Date of Patent: Nov. 4, 2014

(54) ***SANSEVIERIA* PLANT NAMED 'TYLER'**

(50) Latin Name: *Sansevieria trifasciata*
Varietal Denomination: Tyler

(71) Applicant: Florica Farms, Inc., Eustis, FL (US)

(72) Inventor: Marvin Gonzalez Villegas, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 2 days.

(21) Appl. No.: 13/694,852

(22) Filed: Jan. 11, 2013

(65) Prior Publication Data

US 2014/0201877 P1 Jul. 17, 2014

(51) Int. Cl.
*A01H 5/00* (2006.01)

(52) U.S. Cl.
USPC ..... Plt./382

(58) Field of Classification Search
USPC ..... Plt./382
See application file for complete search history.

*Primary Examiner* — Anne Grunberg
(74) *Attorney, Agent, or Firm* — Foley & Lardner LLP

(57) ABSTRACT

The variety 'Tyler' belongs to the compact *Sansevierias* group, with a height of 40 cm, and an average of 7 leaves per plant. The plant shape is an inverted triangle shape and the arrangement of the leaves is in the form of a rosette. Shows vivid green color in the center of the blades alternating with light yellowish green broad bands and narrow brilliant yellowish green margins. One remarkable trait of 'Tyler' is the flower, which shows downwards curved petals.

4 Drawing Sheets

Latin name of the genus and species of the claimed plant: *Sansevieria trifasciata.*

Variety denomination: Tyler.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name "Tyler".

*Sansevieria* is a monocotyledonous and succulent flowering plant, which can be produced in either hard-leafed or soft-leafed varieties. for interior use as a house plant or outdoor as an ornamental plant.

The new *Sansevieria* 'Tyler' originated from a naturally-occurring mutation of the *Sansevieria* variety 'Robusta' (unpatented). The new *Sansevieria* variety 'Tyler' was discovered and selected by the inventor, Marvin Gonzalez Villegas, as a single sprouting rare plant in a 'Robusta' plantation, a controlled environment, in 2007 in Monterrey, San Carlos, province Alajuela, Costa Rica.

Asexual reproduction of the new *Sansevieria* cultivar by vegetative cuttings was first performed in January 2008 in Monterrey, San Carlos, Alajuela, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Tyler', which in combination distinguish this *Sansevieria* as a new and distinct cultivar:

1. Green vivid coloration (RHS 134A) in the interior of the leaf blade with light yellowish green (RHS 141C) margins in both sides of the leaf (4-5 mm).
2. Wide, long lanceolated leaves supported in a rosette.
3. 40-45 cm plant height.
4. Erect plant habit.
5. Needs little water and is very drought tolerant.

The new variety 'Tyler' is considered a variety of *Sansevieria* in the group known as "compact *Sansevieria* plants". The claimed variety 'Tyler' presents an average of 6-7 leaves per plant when it reaches its maturity (between 7-8 months). The claimed variety 'Tyler' has an erect growth habit and the entire plant can reach a height range between 40-45 cm. The leaves are wide (8.5 cm average measured at the widest part of the mature leaf) and lanceolated, with a soft waxy texture and the blades are thin and slightly wavy. The plant has an inverted triangle shape. The younger leaves show a green vivid coloration (RHS 134A) in the interior of the leaf blade. This area shows also irregular streaks or light yellowish-green bands (RHS 145D). There are margins in both sides of the leaf (4-5 mm) which are light yellowish green (RHS 141C). When the leaf is mature the deep color inside turns strong yellowish green (RHS 141), while margins alternate brilliant yellowish green (RHS 154B) and light yellowish-green (RHS 145C) colors. The claimed variety is moderately drought tolerant and adapts to conditions of light and shade (interior and exterior).

The variety 'Robusta' gave rise to the variety 'Tyler'. The 'Robusta' variety is also considered part of the "compact *Sansevierias*" group. 'Tyler' shows more vigor than 'Robusta' but has an equal number of leaves per plant (6-7), with an average width of 8.5 cm (measured in the middle of the mature leaf).

Plants of the new *Sansevieria* 'Tyler' differ from plants of the parental cultivar, 'Robusta' (unpatented) in the characteristics described in Table 1.

TABLE 1

Comparison between new cultivar 'Tyler' and its parent variety 'Robusta'.

| Characteristic | New variety 'Tyler' | Parent variety 'Robusta' (unpatented) |
|---|---|---|
| Plant Vigor | more vigorous | less vigorous |
| Color | variegated leaves (green vivid cross-banding alternating with light yellowish-green bands) and light yellowish margins | variegated leaves (green vivid cross-banding alternating with pale green ones) and yellowish margins. |
| Shape | wide and lanceolated leaves on a rosette | wide and lanceolated leaves on a rosette |
| Texture of leaves | smooth-textured leaves | smooth-textured leaves |

Of the many commercial cultivars known to the present inventor, the most similar in comparison to the new *Sansevieria* 'Tyler' is the parental variety 'Robusta' (unpatented).

BRIEF DESCRIPTION OF THE PHOTOGRAPHS

The accompanying photographs illustrate the overall appearance of the new *Sansevieria* cultivar 'Tyler' showing the colors as true as is reasonably possible with colored reproductions of this type. Colors in the photographs may differ slightly from the color value cited in the detailed botanical description which accurately describe the color of 'Tyler'.

DETAILED BOTANICAL DESCRIPTION

Figure 1:
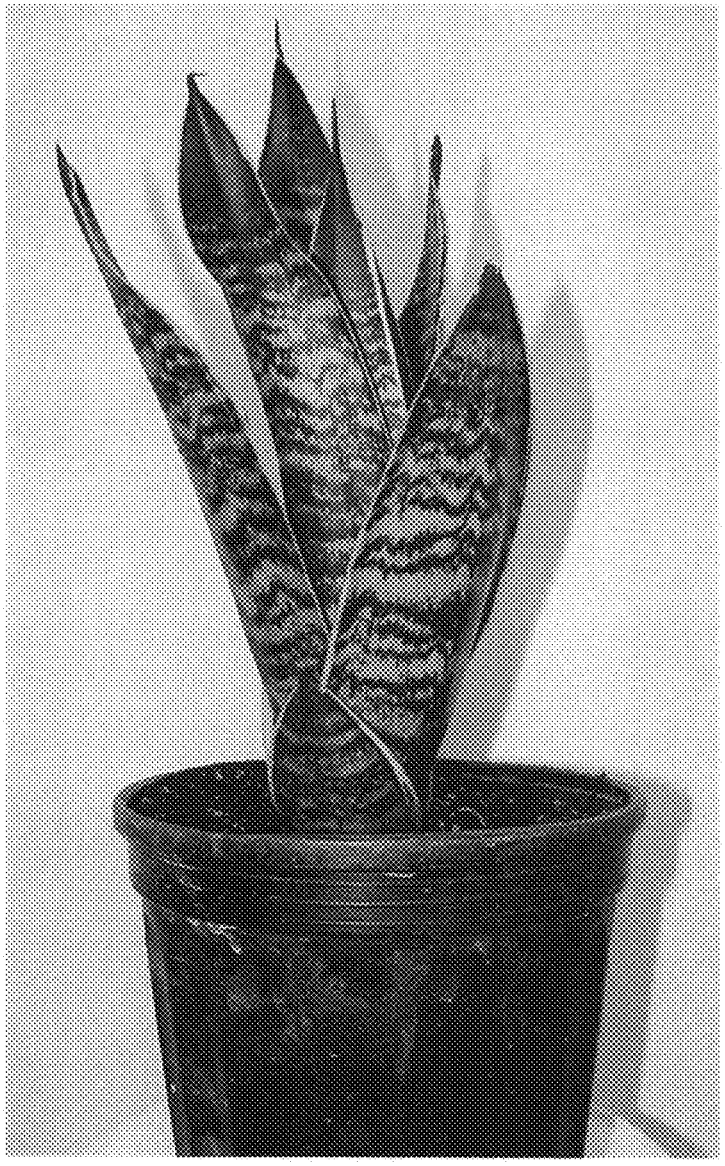
FIG. 1 shows a side view of an eight month old plant of *Sansevieria* 'Tyler' in a 21 cm diameter pot.
Figure 2:
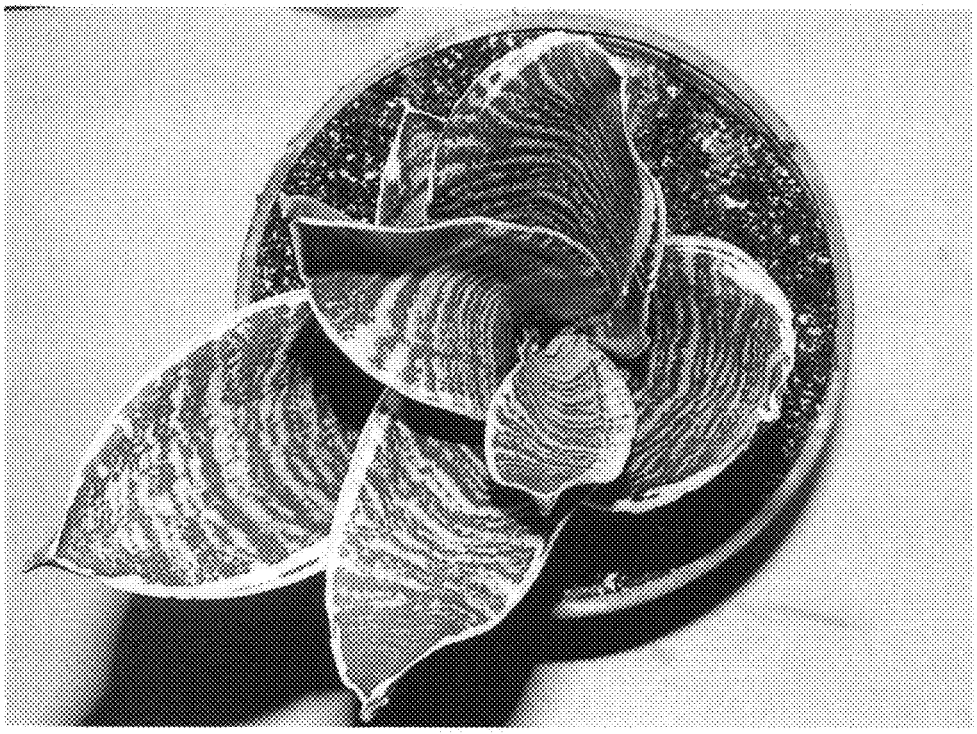
FIG. 2 shows a top view of an eight month old plant of *Sansevieria* 'Tyler' in a 21 cm diameter pot.
Figure 3:
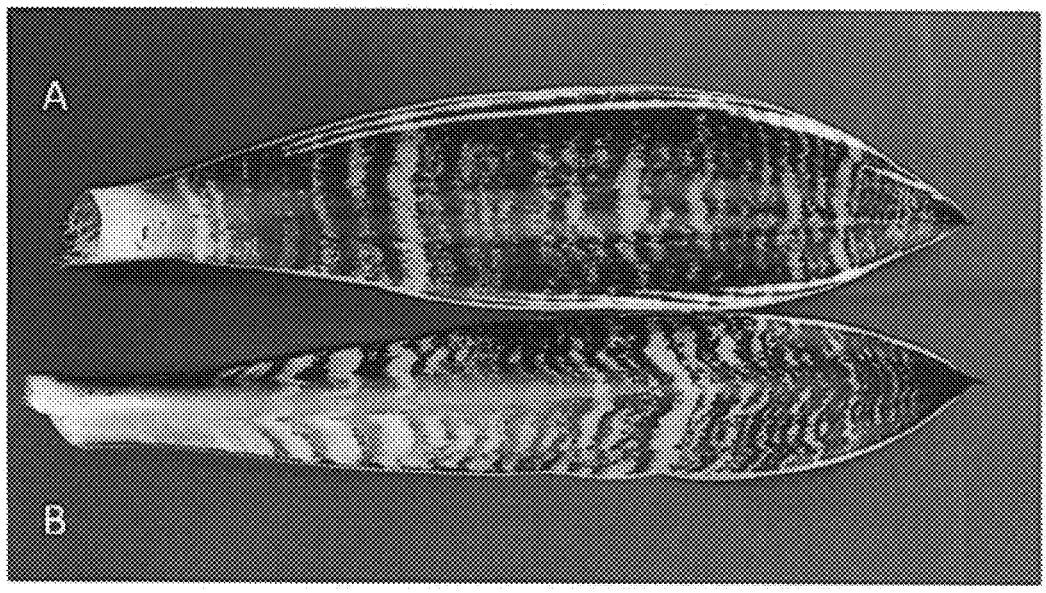
FIG. 3 shows a close up view of the typical leaves of 'Tyler' (Upper side: A, under side: B) from an eight month old plant.

The new *Sansevieria* 'Tyler' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'Tyler' as grown in an open field at Monterrey, San Carlos de Alajuela province, Costa Rica, conditions which closely approximate those generally used in commercial practice. Average temperature at Monterrey is 24.5° C. during the day and 18° C. at night. Plants grow under natural light conditions.

This crop does not require constant fertilization, to increase production per area about 200 kg $ha^{-1}$ N, 150 kg $ha^{-1}$ of P and 100 kg $ha^{-1}$ K are required, the production is closely related with soil conditions in which they are grown.

Color references are made to The Royal Horticultural Society Colour Chart (R.H.S.), (April 2009) except where general colors of ordinary significance are used. The photographs and descriptions were taken during the rainy season in Monterrey, San Carlos, Alajuela province, Costa Rica when outdoor day temperature was 23° C. The age of the plants described is 8 months.

Classification:

*Botanical.*—*Sansevieria trifasciata.*

*Variety denomination.*—Tyler.

Parentage: *Sansevieria trifasciata* 'Robusta' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to a low temperature of about 12° C. and tolerant to a high temperature of about 35° C.

*Fertilization.*—200, 150 and 100 kg $ha^{-1}$ de N, P and K.

*Growth regulators.*—Not necessary.

Propagation:

*Type.*—Vegetative, by rooted cuttings.

*Rooting habit and description.*—Rizomes, with short roots.

*Time to initiate roots.*—About 15 to 22 days at 20-25° C.

*Time to produce a rooted cutting.*—About 60 to 90 days.

Plant:

*General appearance and form.*—Height: About 40 cm when grown in ground; about 35 cm when grown in a 21 cm size container. Spread: About 15 cm when grown in ground; About 10 cm when grown in 21 cm size container. Form: Monocot; leaf bases arranged in a rosette around growing point. Shape: inverted triangle.

*Growth rate and habit.*—About 2 cm per week; upright.

*Fragrance.*—None.

*Stem.*—Modified (Rizoma and foliage). Length: About 9 cm when grown in ground; About 8 cm when grown in 21 cm size container. Diameter: About 2 cm to 3.5 cm. Shape: round. Texture: Rough. Color: RHS 17A. Strength: strong and durable. Internode length: About 1 mm to 3 mm.

Foliage:

*Quantity.*—About 7.

*Arrangement and attachment.*—Single, alternate; leaf bases arranged in a rosette around growth point.

*Leaf length.*—About 40 cm.

*Leaf width.*—About 8.5 cm.

*Overall shape of leaf.*—Lanceolated.

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None.

*Color of mature leaf.*—Upper Surface: RHS 134A with bands of RHS 145 D, margins RHS 141C. Lower Surface: RHS 134A with bands of RHS 142 D, margins RHS 141C.

*Color of immature leaf.*—Upper Surface: RHS 134A with bands of RHS 145 D, margins RHS 141C. Lower Surface: RHS 134A with bands of RHS 142 D, margins RHS 141C.

*Venation.*—Pattern: longitudinal/parallel leaf shape. Color: None. Leaf fragrance: None.

Inflorescence description:

*Arrangement and type.*—Inflorescence.

*Orientation at opening.*—Out of the spike.

*Quantity.*—Per Plant with at least one open flower: One inflorescence per plant. The inflorescence opened 2 weeks after appearance of the spike.

*Inflorescence size.*—Length: About 27 cm. Diameter: About 3.5 cm.

*Flower size*.—Length: About 2.2 cm. Diameter: About 1 cm. Depth: About 1 cm.

*Fragrance*.—Soft and pleasant.

*Bud*.—Rate of opening: About 7 to 8 days, according to weather. Shape: long. Length: About 22 mm. Diameter: About 4 mm. Color: Apex: RHS 142D. Base: RHS 145D. Texture (both surfaces): smooth.

Petals:

*Quantity*.—6.

Figure 4:
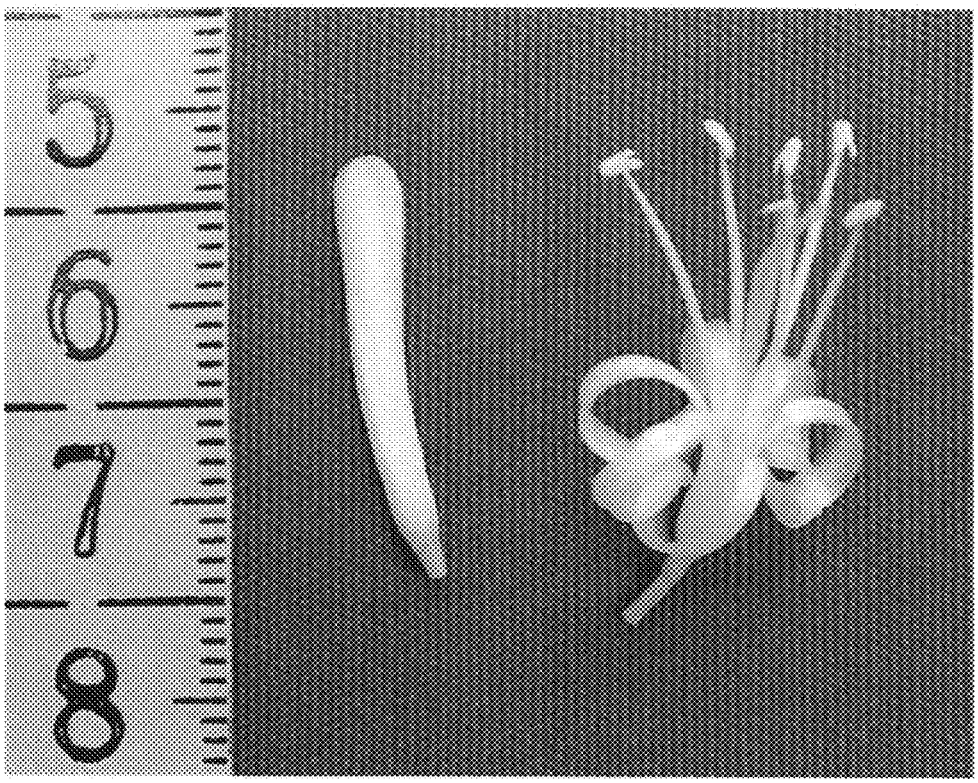
FIG. 4 shows a typical bud and opened flower of *Sansevieria* 'Tyler'.

*Arrangement*.—Radial-shaped and curved downwards (see FIG. 4).

Reproductive organs:

*Androecium*.—Stamen: Number: 6 per flower. Length: About 1.5 cm. Color: RHS 155D. Anther: Length: About 2 mm. Width : About 1 mm. Color: RHS 145D. Filament: Length: About 1.3 cm. Color: RHS 155D. Pollen: Amount: moderate. Color: RHS 154D.

*Gynoecium*.—Pistil: Number: One per flower. Length: About 2.5 cm. Stigma: Length: About 1 mm. Width: About 0.8 mm. Color: RHS 155D. Style: Length: About 1.9 cm. Color: RHS 155D. Ovary: Length: About 5 mm. Width: About 2.5 mm. Color: RHS 1D.

Weather resistance: Drought tolerant.

Fruit: None Observed.

Seeds: None Observed.

Disease/pest resistance: Not observed for disease/pest resistance.

Disease/pest susceptibility: Not observed for disease/pest susceptibility.

I claim:

1. A new and distinct *Sansevieria* plant named 'Tyler', substantially as illustrated and described herein.

* * * * *